US008607623B2

(12) United States Patent
Ciaravino et al.

(10) Patent No.: US 8,607,623 B2
(45) Date of Patent: Dec. 17, 2013

(54) METHOD FOR BIODIESEL BLENDING DETECTION BASED ON FUEL POST-INJECTION QUANTITY EVALUATION

(75) Inventors: Claudio Ciaravino, Turin (IT); Giovanna Massetti, Moconesi (IT)

(73) Assignee: GM Global Technology Operations LLC, Detroit, MI (US)

( * ) Notice: Subject to any disclaimer, the term of this patent is extended or adjusted under 35 U.S.C. 154(b) by 26 days.

(21) Appl. No.: 13/473,740

(22) Filed: May 17, 2012

(65) Prior Publication Data
US 2012/0291529 A1 Nov. 22, 2012

(30) Foreign Application Priority Data
May 19, 2011 (GB) .................................. 1108413.4

(51) Int. Cl.
*G01M 15/04* (2006.01)

(52) U.S. Cl.
USPC ..................... 73/114.01; 73/35.02; 73/114.38

(58) Field of Classification Search
USPC ................................ 73/35.02, 114.01, 114.38
See application file for complete search history.

(56) References Cited

U.S. PATENT DOCUMENTS

| | | | | |
|---|---|---|---|---|
| 7,607,422 B2* | 10/2009 | Carlson et al. | ................. | 123/672 |
| 8,042,384 B2* | 10/2011 | Bailey | ......................... | 73/114.38 |
| 8,046,153 B2* | 10/2011 | Kurtz et al. | ................... | 701/103 |
| 8,068,971 B2* | 11/2011 | Hamedovic et al. | .......... | 701/103 |
| 8,073,638 B2* | 12/2011 | Birk et al. | ......................... | 702/30 |
| 8,302,578 B2* | 11/2012 | Schneider et al. | ......... | 123/196 R |
| 2009/0105965 A1* | 4/2009 | Birk et al. | ........................ | 702/30 |
| 2011/0093181 A1* | 4/2011 | Ciaravino et al. | ............. | 701/102 |
| 2011/0125383 A1* | 5/2011 | Vassallo et al. | ................. | 701/99 |
| 2011/0166767 A1* | 7/2011 | Kurtz et al. | .................... | 701/103 |
| 2011/0208409 A1* | 8/2011 | Snyder et al. | ................. | 701/109 |

FOREIGN PATENT DOCUMENTS

| | | | |
|---|---|---|---|
| EP | 1757791 A3 | 12/2009 | |
| GB | 2474512 A | 4/2011 | |
| GB | 2474513 A | 4/2011 | |
| JP | 2008274891 A | 11/2008 | |
| WO | 2010015002 A2 | 2/2010 | |

\* cited by examiner

*Primary Examiner* — Freddie Kirkland, III
(74) *Attorney, Agent, or Firm* — Ingrassia Fisher & Lorenz, P.C.

(57) ABSTRACT

A method for detecting the blending level of biodiesel fuel in an internal combustion engine includes setting at least two post injection fuel quantity reference values respectively for known biodiesel blending percentage levels. A post injection fuel quantity value is evaluated and is compared with the at least two post injection fuel quantity reference value. A predetermined correlation set of values between the post injection fuel quantity value and a biodiesel blending level expressed by biodiesel percentage with respect to the petrodiesel is used to determine the biodiesel blending level.

20 Claims, 4 Drawing Sheets

| Properties | Diesel | RME Biodiesel | JME Biodiesel |
|---|---|---|---|
| Carbon content C [w%] | 86.5 | 79.6 | 79.7 |
| Hydrogen content H [w%] | 13.5 | 12.1 | 12.2 |
| Oxygen content O [w%] | - | 8.3 | 8.1 |
| Sulfur content S [ppm] (EN ISO 14596-98) | < 10 | < 10 | < 10 |
| Stoichiometric ratio $(A/F)_{st}$ | 14.4 | 13.0 | 13.0 |
| Net Heating Value LHV [KJ/Kg] (ASTM D 240-00) | 42960 | 37365 | 37455 |
| Cetane Number (ISO 5165-98) | 51.8 | 51.5 | 56.6 |
| Density at 15°C [Kg/m$^3$] | 840 | 883 | 880 |
| Viscosity at 20°C [mm$^2$/s] | 3.14 | 7.09 | 7.00 |
| LHV/$(A/F)_{st}$ [MJ/Kg] | 2.99 | 2.88 | 2.88 |

Fig. 1

| Fuel Blending level [%] (Bxx) | Engine Speed | bmep | Indicated torque | T inlet DPF ($Tin_{REF}$) | Post Injection Fuel Quantity ($Q_{Bxx}$) |
|---|---|---|---|---|---|
| | [rpm] | [bar] | [Nm] | [°C] | [mm3] |
| B5 | 2000 | 5 | 71,5 | 630 | 5,77 |
| B30 | 2000 | 5 | 76,9 | 630 | 7,05 |
| B100 | 2000 | 5 | 85 | 630 | 10,9 |

METHOD FOR BIODIESEL BLENDING DETECTION BASED ON FUEL POST-INJECTION QUANTITY EVALUATION

CROSS-REFERENCE TO RELATED APPLICATION

This application claims priority to British Patent Application No. 1108413.4, filed May 19, 2011, which is incorporated herein by reference in its entirety.

TECHNICAL FIELD

The technical field generally relates to methods for biodiesel blending detection based on the fuel post injection quantity evaluation by the electronic control unit (ECU) of a vehicle. In particular, the technical field relates to a method for detecting the blending level of biodiesel fuel by evaluating the fuel post injection quantity requested during the regeneration phase of the diesel particulate filter (DPF) mounted on the vehicle.

BACKGROUND

Biodiesel can be used in modern diesel engines in pure form or may be blended with petroleum diesel (petro-diesel) at any concentration.

It has to be noted that the biodiesel blending level is commonly expressed by means of the biodiesel percentage with respect to the petro-diesel. Usually the expression Bxx is used to indicate the biodiesel blending level, wherein the term "xx" is the biodiesel percentage with respect to the petro-diesel. In other words, a biodiesel blend with 30% of biodiesel is indicated as B30. Obviously, B0 is petro-diesel, while B100 indicates a biodiesel fuel without petro-diesel.

Using biodiesel may have positive effects such as particulate reduction, possibility of reduction of the regeneration frequency of the diesel particulate filter (DPF), etc., and also negative effects such as increased nitrogen oxides emission and increased oil dilution.

Both positive and negative effects deriving from the use of a biodiesel are strictly related to the amount of biodiesel into the fuel, i.e. the biodiesel percentage with respect to the petro-diesel. For example, the higher distillation curve of the biodiesel reduces the amount of the fuel that evaporates, and for this reason the amount of the biodiesel in liquid phase injected into the cylinder increases enormously.

The higher amount of biodiesel in liquid phase into the cylinder causes the passage into the cylinder liner, which leads to an increasing of the oil dilution. As verified by the applicant by means of experimental tests, i.e. run at 2000×5 [rpm×bmep] which consist of 20 repeated complete regeneration cycles, with a 5% of biodiesel (B05) the fuel dilution in oil is roughly 0.3% of the total oil mass per regeneration cycle. With 100% of biodiesel (B100) the fuel dilution in oil is roughly 1% of the total oil mass per regeneration cycle.

For these and other reasons there is the need to determine the actual biodiesel percentage that expresses the biodiesel blending.

The pending patent applications GB0918272.6 and GB0918273.4, in the name of GM Global Technology Operations Inc., disclose two methods for detecting the biodiesel blending respectively based on the evaluation of the mean effective pressure and of the relative air-to-fuel ratio.

It is at least one object herein to provide an alternative method for detecting the biodiesel percentage into the fuel that expresses the biodiesel blending level. In addition, other objects, desirable features and characteristics will become apparent from the subsequent summary and detailed description, and the appended claims, taken in conjunction with the accompanying drawings and this background.

SUMMARY

In accordance an exemplary embodiment, a method for biodiesel blending detection includes:
a) setting at least two post injection fuel quantity reference values respectively for known biodiesel blending percentage levels;
b) evaluating a post injection fuel quantity value;
c) comparing the post injection fuel quantity value with the at least two post injection fuel quantity reference values; and
d) using a predetermined correlation set of values between the post injection fuel quantity value and a biodiesel blending level expressed by biodiesel percentage with respect to the petro-diesel in order to determine the biodiesel blending level.

In one embodiment, the evaluation of the post injection fuel quantity value is carried out during the regeneration phase of a diesel particulate filter (DPF) connected to the engine in order to evaluate the fuel post injection quantity requested for reaching the desired temperature value at the inlet of the DPF. It is possible to determine the blending level during the regeneration phase of the diesel particulate filter DPF by comparing the fuel post injection quantity requested for reaching the desired temperature value at the inlet of the DPF necessary for carrying out an efficient regeneration phase with at least two post injection fuel quantity reference values calibrated for known blending levels of biodiesel. By this method the biodiesel percentage in the fuel can be detected with no extra components using the information already available, and thus without extra costs.

Since the post injection fuel quantity value requested during the regeneration phase of the DPF for reaching the desired temperature value is sensitive to the biodiesel percentage, its comparison with at least two post injection fuel quantity reference values calibrated for known blending levels permits detecting the biodiesel percentage that expresses the actual biodiesel blending level of the fuel used in the vehicle.

As mentioned above, the method includes using a predetermined correlation set of values between the post injection fuel quantity value and a biodiesel blending level expressed by biodiesel percentage with respect to the petro-diesel in order to determine the actual biodiesel blending level. In particular, the predetermined correlation of set of values is substantially linear in order to allow interpolation of values.

In an embodiment, the reference values are post injection fuel quantity values calibrated for known biodiesel blending levels of 5% and 100%, expressed in percentages with respect to the petro-diesel. Thus, by comparing the evaluated post injection fuel quantity requested during the regeneration phase of the DPF with the two reference values, and in particular by executing a linear interpolation of values, it is possible to determine the actual blending level of the fuel.

In another embodiment, a computer program includes computer executable codes for carrying out the method for detecting the blending level of biodiesel, described above. The computer program, stored in a computer readable medium, includes: a computer executable code for setting at least two post injection fuel quantity reference values respectively for known biodiesel blending levels, a computer executable code for evaluating a post injection fuel quantity value, a computer executable code for comparing the post injection fuel quantity value with the at least two post injection fuel quantity reference values, and computer executable code for using a predetermined correlation set of values between the post injection fuel quantity value and a biodiesel blending level expressed by biodiesel percentage with respect to the petro-diesel in order to determine the biodiesel blending level.

BRIEF DESCRIPTION OF THE DRAWINGS

The various embodiments will hereinafter be described in conjunction with the following drawing figures, wherein like numerals denote like elements, and wherein:

FIG. 1 is a table showing a comparison of some chemical properties of biodiesel and petro-diesel;

DETAILED DESCRIPTION

The following detailed description is merely exemplary in nature and is not intended to limit the various embodiments or the application and uses thereof Furthermore, there is no intention to be bound by any theory presented in the preceding background or the following detailed description.

A method for detecting the blending level of biodiesel fuel in an internal combustion engine 110 is based on the comparison of a post injection fuel quantity value QBxx with at least two post injection fuel quantity reference values QREF', QREF" respectively calibrated for known biodiesel blending percentage levels. In accordance with an exemplary embodiment, the evaluation of the post injection fuel quantity value QBxx is carried out during the regeneration phase of a diesel particulate filter DPF connected to the engine.

Figure 4:
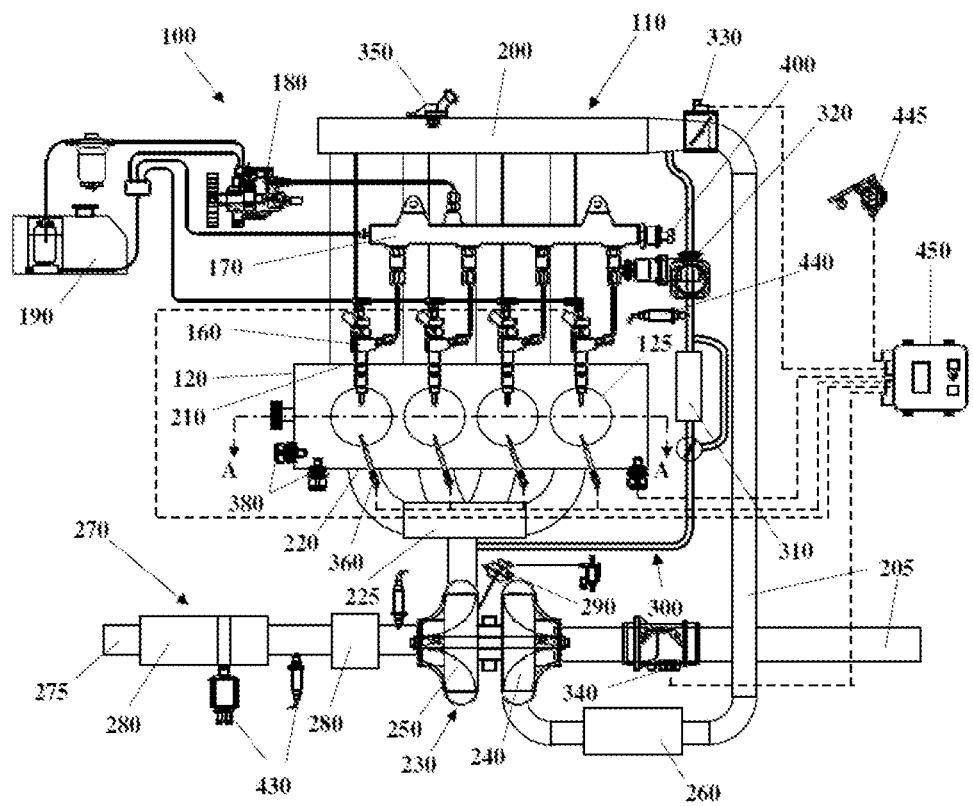
FIGS. 4 and 5 show possible embodiments of an automotive system.
Figure 5:
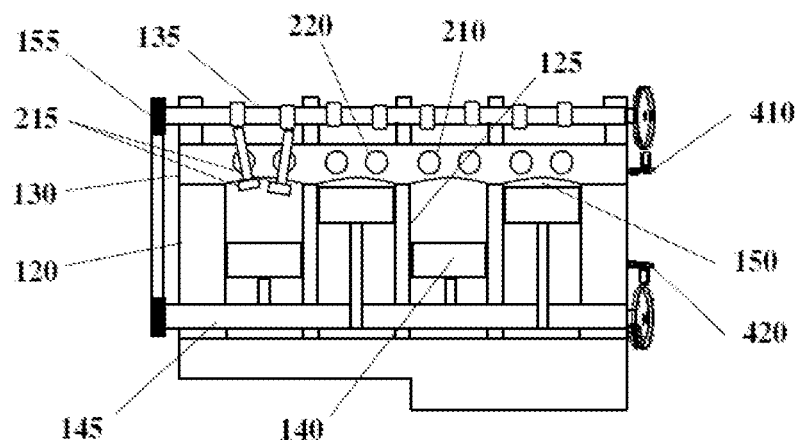

FIGS. 4 and 5 show some embodiments of an automotive system 100 that includes an internal combustion engine (ICE) 110 having an engine block 120 defining at least one cylinder 125 having a piston 140 coupled to rotate a crankshaft 145. A cylinder head 130 cooperates with the piston 140 to define a combustion chamber 150. A fuel and air mixture (not shown) is disposed in the combustion chamber 150 and ignited, resulting in hot expanding exhaust gasses causing reciprocal movement of the piston 140. The fuel is provided by a fuel injector 160 and the air through an intake port 210. The fuel is provided at high pressure to the fuel injector 160 from a fuel rail 170 in fluid communication with a high pressure fuel pump 180 that increases the pressure of the fuel received from a fuel source 190. Each of the cylinders 125 has at least two valves 215, actuated by a camshaft 135 rotating in time with the crankshaft 145. The valves 215 selectively allow air into the combustion chamber 150 from the port 210 and alternately allow exhaust gases to exit through a port 220. In some examples, a cam phaser 155 may selectively vary the timing between the camshaft 135 and the crankshaft 145.

The air may be distributed to the air intake port(s) 210 through an intake manifold 200. An air intake duct 205 may provide air from the ambient environment to the intake manifold 200. In other embodiments, a throttle body 330 may be provided to regulate the flow of air into the manifold 200. In still other embodiments, a forced air system such as a turbocharger 230, having a compressor 240 rotationally coupled to a turbine 250, may be provided. Rotation of the compressor 240 increases the pressure and temperature of the air in the duct 205 and manifold 200. An intercooler 260 disposed in the duct 205 may reduce the temperature of the air. The turbine 250 rotates by receiving exhaust gases from an exhaust manifold 225 that directs exhaust gases from the exhaust ports 220 and through a series of vanes prior to expansion through the turbine 250. The exhaust gases exit the turbine 250 and are directed into an exhaust system 270. This example shows a variable geometry turbine (VGT) with a VGT actuator 290 arranged to move the vanes to alter the flow of the exhaust gases through the turbine 250. In other embodiments, the turbocharger 230 may be fixed geometry and/or include a waste gate.

The exhaust system 270 may include an exhaust pipe 275 having one or more exhaust aftertreatment devices 280. The aftertreatment devices may be any device configured to change the composition of the exhaust gases. Some examples of aftertreatment devices 280 include, but are not limited to, catalytic converters (two and three way), oxidation catalysts (such as diesel oxidation catalyst DOC), lean NOx traps, hydrocarbon adsorbers, selective catalytic reduction (SCR) systems, and particulate filters (such as diesel particulate filter DPF). Other embodiments may include an exhaust gas recirculation (EGR) system 300 coupled between the exhaust manifold 225 and the intake manifold 200. The EGR system 300 may include an EGR cooler 310 to reduce the temperature of the exhaust gases in the EGR system 300. An EGR valve 320 regulates a flow of exhaust gases in the EGR system 300.

The automotive system 100 may further include an electronic control unit (ECU) 450 in communication with one or more sensors and/or devices associated with the ICE 110. The ECU 450 may receive input signals from various sensors configured to generate the signals in proportion to various physical parameters associated with the ICE 110. The sensors include, but are not limited to, a mass airflow and temperature sensor 340, a manifold pressure and temperature sensor 350, a combustion pressure sensor 360, coolant and oil temperature and level sensors 380, a fuel rail pressure sensor 400, a cam position sensor 410, a crank position sensor 420, exhaust pressure and temperature sensors 430, an EGR temperature sensor 440, and an accelerator pedal position sensor 445. Furthermore, the ECU 450 may generate output signals to various control devices that are arranged to control the operation of the ICE 110, including, but not limited to, the fuel injectors 160, the throttle body 330, the EGR Valve 320, the VGT actuator 290, and the cam phaser 155. Note, dashed lines are used to indicate communication between the ECU 450 and the various sensors and devices, but some are omitted for clarity.

Turning now to the ECU 450, this apparatus may include a digital central processing unit (CPU) in communication with a memory system and an interface bus. The CPU is configured to execute instructions stored as a program in the memory system, and send and receive signals to/from the interface bus. The memory system may include various storage types including optical storage, magnetic storage, solid state storage, and other non-volatile memory. The interface bus may be configured to send, receive, and modulate analog and/or digital signals to/from the various sensors and control devices. The program may embody the methods disclosed herein, allowing the CPU to carryout the steps of such methods and control the ICE 110.

As already mentioned above, according to the various embodiments of the method contemplated herein, the detection of the blending level of biodiesel fuel is based on the comparison of a post injection fuel quantity value QBxx with at least two post injection fuel quantity reference values QREF', QREF" respectively calibrated for known biodiesel blending percentage levels. It has to be noted that term "fuel post injection quantity" is used herein to indicate after or post injection fuel quantity, that it is added to the standard injection path (and in general to the torque forming injection) in some conditions, for example during the regeneration phase of the diesel particulate filter DPF.

In fact, when the soot stored in the filter reaches a predetermined level or, according to some regeneration strategies control, there is the need to regenerate the filter by carrying out the complete oxidation of the soot stored therein. Therefore, there is the need to increase the exhaust temperature in order to reach a predetermined temperature at the inlet of the DPF TinREF necessary for obtaining an efficient regeneration.

In fact, a specific temperature value, in a predetermined temperature range, is necessary to ensure the complete oxidation of the soot accumulated in the filter without damaging its substrate. More in detail, the exhaust temperature is increased until a temperature desired value TinREF, or temperature set point, at the inlet of the DPF is reached. Therefore, to reach the desired temperature value TinREF during the regeneration phase of the DPF, the fuel post injection quantity is added to the standard injection path to increase the exhaust temperature.

Generally, a control strategy of the post injection management during the regeneration phase of the DPF comprises a modification (correction) of the fuel post injection quantity value on the base of a measured value of the temperature at the inlet of the DPF TinMEAS.

In fact, during the DPF regeneration the fuel post injection quantity requested is the result of two main contributions, i.e. a base map fuel post injection quantity value QMAP, measured and/or estimated through a map function of engine speed and the indicated brake torque, and a correction value QCORR based on the difference between the inlet temperature desired value TinREF, which is the desired temperature value necessary for carrying out the regeneration process, and the current measured value of the temperature at the inlet of the DPF TinMEAS.

Figure 6:
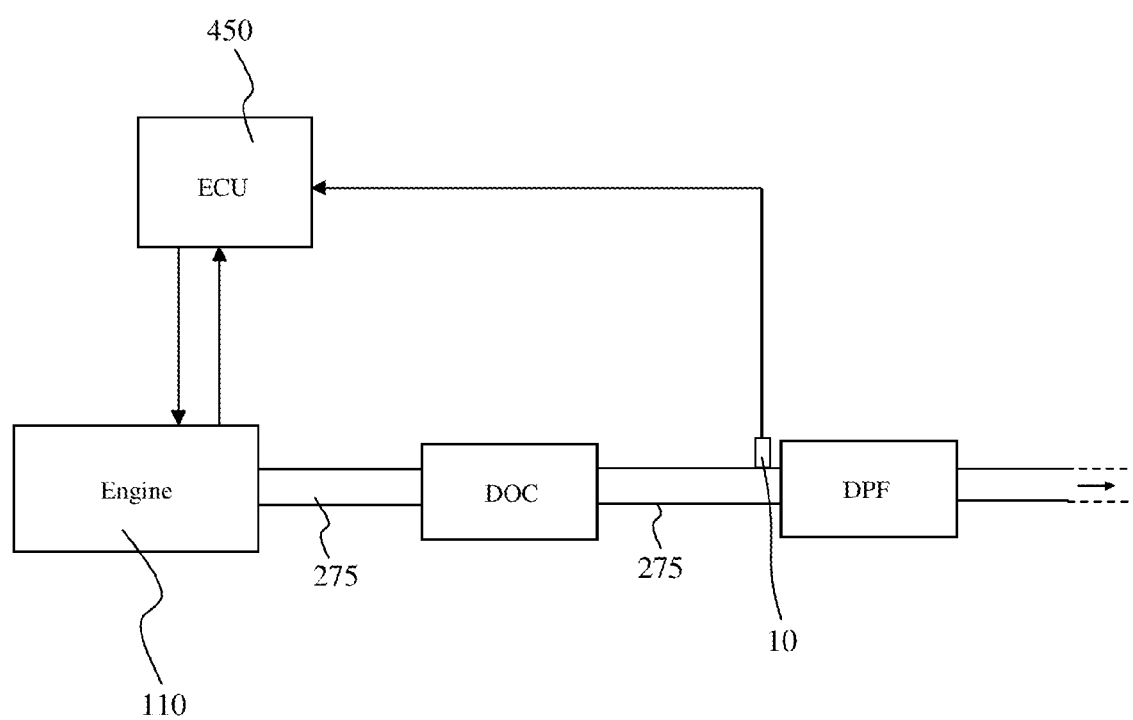
FIG. 6 is a simplified block diagram of an automotive system including an internal combustion engine and a diesel particulate filter (DPF) wherein is used the method according to an exemplary embodiment.

In FIG. 6 is shown a simplified scheme of an automotive system provided with an internal combustion engine 110 and a diesel particulate filter DPF. Preferably the inlet temperature value TinMEAS is measured by means of a sensor 10 placed at the inlet of the DPF. Alternatively, the inlet temperature value TinMEAS can be measured with another temperature sensor, for example the exhaust temperature sensor 430. It has to be noted that, in the possible configuration of the automotive system shown in FIG. 6, exhaust gases are discharged trough an exhaust pipe 275 which connects the engine to a diesel oxidation catalyst (DOC) and then to a diesel particulate filter DPF.

When a biodiesel fuel is used, its different properties, such as lower heating value, higher density and viscosity, and different distillation curve leads to an increased fuel post injection quantity required to reach the exhaust temperature, and in particular the desired temperature at the inlet of the DPF TinREF necessary for allowing an efficient and complete soot oxidation and DPF regeneration.

FIG. 1 is a table showing a comparison of some chemical properties of two biodiesel types, namely RME (biodiesel produced from low crucic acid varieties of canola seed) and JME (Biodiesel produced from jatropha), and the petro-diesel.

In particular, due to different chemical properties of biodiesel with respect to the petro-diesel, the correction value of the post injection fuel quantity QCORR increases.

More in detail, the higher viscosity of biodiesel leads to a reduction of the injected quantity (in volume) for the same energizing time, that is partially compensated by the higher density that increase the amount mass per unit volume. The lower fuel mass injected combined with the lower heating value of biodiesel leads to a reduced amount of chemical energy introduced into the combustion chamber. The effect is a reduced exothermal energy generated into the diesel oxidation catalyst DOC providing a lower increasing of the exhaust temperature at the DPF inlet.

For these reasons there is the need to increase the fuel post injection quantity during the regeneration phase in order to reach the desired temperature value TinREF at the inlet of the DPF for allowing an optimal regeneration and the complete oxidation of soot accumulated into the particulate filter.

More in detail, according to an embodiment, the blending level is determined during the regeneration phase of the DPF by comparing the fuel post injection quantity QBxx requested for reaching the desired temperature value at the inlet of the DPF TinREF necessary for carrying out an efficient regeneration, with at least two post injection fuel quantity reference values QREF', QREF" calibrated respectively for known blending levels of biodiesel.

In-house tests demonstrates that the post injection fuel quantity necessary for reaching the desired temperature at the inlet of the PDF TinREF is higher with respect to the post injection fuel quantity required when petro-diesel is used for the reason reported above, and in particular of the lower exhaust temperature. In particular, experimental data shows that the post injection fuel quantity value QBxx is proportional to the biodiesel blending level Bxx and change linearly with the biodiesel blending level.

Figures 2, 3:
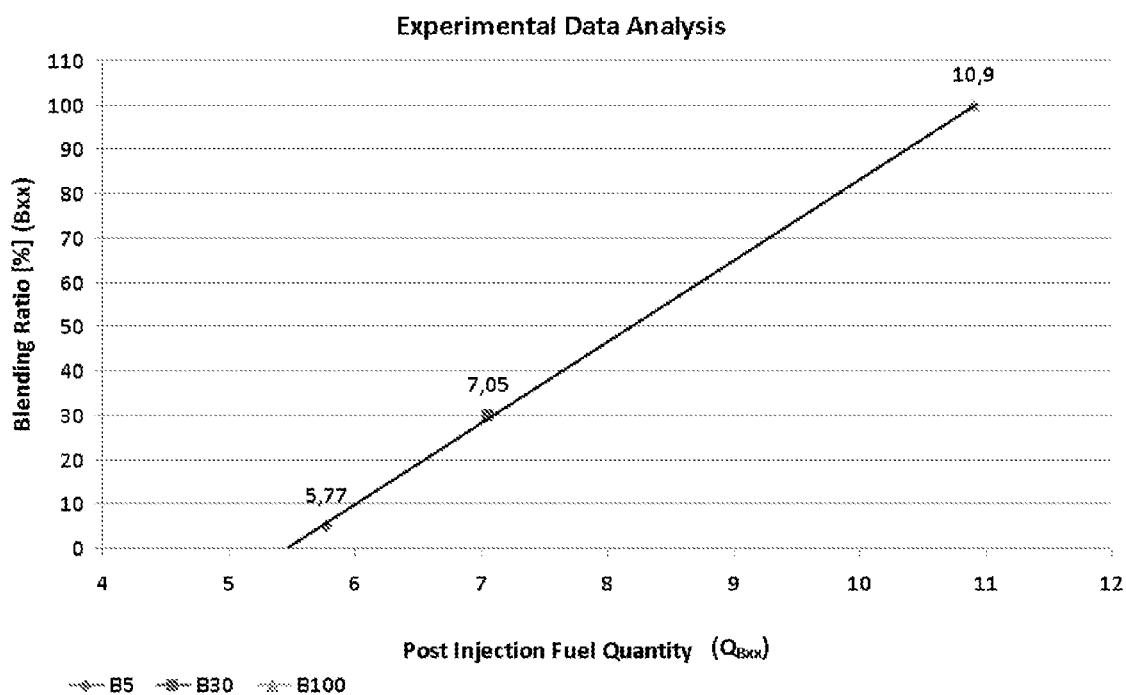
FIG. 2 is a table of experimental data relating to the evaluation of the post injection fuel quantity during the regeneration phase of the DPF with different biodiesel blending levels.
FIG. 3 is a graphical representation of the experimental data of FIG. 2.

The table of FIG. 2 shows experimental data performed on a 1.3 L engine during the regeneration phase of the DPF for a particular working point, i.e. at 2000 rpm and 5 bmep (usually indicated as 2000×5), i.e. the post injection fuel quantity value QBxx with different blending level of biodiesel, namely B5, B30 and B100.

As shown in FIG. 3, which is a graphical representation of the experimental data shown in the table of FIG. 2, the post injection fuel quantity QBxx varies substantially linearly with the blending level of biodiesel Bxx.

It has to be noted that in FIG. 3 and in the table 2 the post injection fuel quantity QBxx is the sum of two contributions, i.e. a base map post injection fuel quantity value QMAP, and a correction post injection quantity value QCORR derived by comparing the inlet temperature desired value TinREF of the diesel particulate filter DPF and the current inlet temperature value TinMEAS of the diesel particulate filter DPF. Obviously, as already stated above, the inlet temperature value TinMEAS can be measured by means of a suitable sensor 10.

According to an embodiment, by setting at least two post injection fuel quantity reference values QREF', QREF" for known biodiesel blending levels and by comparing the post injection fuel quantity value QBxx, which is requested during the regeneration phase of the PDF, with the at least two post injection fuel quantity reference values QREF', QREF" it is possible to determine the actual biodiesel percentage.

According to another embodiment, a correlation of a set of values between the post injection quantity QBxx required for reaching the desired temperature at the inlet of the DPF Tin- REF and the blending level of biodiesel Bxx can be used for detecting the actual blending level of the biodiesel. As already stated above in connection to FIGS. 2 and 3, the predetermined correlation is substantially linear for allowing interpolation of values.

The reference values of the post injection quantity value QREF', QREF" are calibrated for known biodiesel blending levels, i.e. of 5% QREFB05 and 100% QREFB100, expressed in percentages with respect to the petro-diesel. The extreme points of the range ensure higher precision to the detection method because they minimize the weight of the fuel quantity estimation error but it has to be noted that QREF' and QREF" can be calibrated at any known blending level.

Therefore the blending level of the biodiesel is detected by linear interpolation using the formula:

$$B_{XX} = \left( \frac{0.95}{QREF_{B100} - QREF_{B05}} \cdot (Q_{Bxx} - QREF_{B05}) + 0.05 \right) \cdot 100, \quad (1)$$

wherein $Q_{Bxx}$ is the post injection fuel quantity value, evaluated during the regeneration phase of the DPF, and $QREF_{B05}$ and $QREF_{B100}$ are post injection fuel quantity reference values calibrated for known biodiesel blending levels (B05) and (B100).

The above-described method can be repeated continuously in order to achieve a continuous detection of the biodiesel blending level.

Moreover, the method for controlling the blending level of biodiesel fuel in an internal combustion engine may be carried out by a computer program comprising program codes (computer executable codes) for performing the detection steps already described above. The computer program comprises computer executable codes that can be stored on a computer readable medium, or a storage unit, such as CD, DVD, flash memory, hard-disk, or the like. The computer program comprises computer executable code for setting at least two post injection fuel quantity reference values respectively for a known biodiesel blending level; a computer executable code for evaluating a post injection fuel quantity value; a computer executable code for comparing the post injection fuel quantity value with the at least two post injection fuel quantity reference values, and computer executable code for using a pre-determined correlation set of values between the post injection fuel quantity value QBxx and a biodiesel blending level Bxx expressed by percentages with respect to the petro-diesel, in order to determine the biodiesel blending level. As already described above in connection to FIGS. 2 and 3, the correlation of the set of values between the post injection fuel quantity value QBxx and a biodiesel blending level Bxx is substantially linear allowing interpolation of values.

According to an embodiment, the computer program is stored in a storage unit or a computer readable medium which is connected, or integrally produced with an electronic control unit (ECU) 450 for an internal combustion engine (110). The electronic control unit 450 is provided with a digital central processing unit (CPU), or any suitable means known in art, for receiving the computer codes of the computer program and for executing them. Starting from the evaluated post injection fuel quantity QBxx, the ECU 450 compares the latter with two reference value of the post injection fuel quantity QREF', QREF" calibrated for two known blending levels of the biodiesel, preferably B5 and B100. By linear interpolation of the values according to the formula (1), the ECU allows to be detected the biodiesel percentage that expresses the actual biodiesel blending.

The evaluated post injection fuel quantity QBxx requested for increasing the exhaust temperature in order to reach the desired temperature value at the inlet of the DPF necessary for carrying out the regeneration process is the sum of two contributions, i.e. a base map post injection fuel quantity value QMAP and a correction post injection quantity value QCORR derived by comparing the inlet temperature desired value TinREF of the diesel particulate filter DPF and the current inlet temperature value TinMEAS of the diesel particulate filter DPF.

No additional sensors are needed to perform the above described method and there are no related costs to current diesel engine configurations.

Fine-tuning of this strategy and verification of its potentialities will be critical on actual engine hardware, since B30 is already impacting in an appreciable way oil dilution, soot accumulation on DPF, as well as modifying engine-out emissions and performances.

Detecting the biodiesel blending level allows the engine to mitigate emission and performance drift due to different fuel properties and so, potentially, makes the diesel engine functionally completely independent from fuel type without adding any cost.

More in detail, the biodiesel blending detection by the method according to the various embodiments contemplated herein could enable, for example:

tailored oil life monitoring to actual engine fuelling, taking into account that biodiesel requires shorter oil drain intervals;

tailored DPF regeneration strategy;

and also tailored soot accumulation statistical model to actual engine fuelling, taking into account that biodiesel could enable longer intervals between DPF regenerations; and calibration optimizations with performance compensation.

While at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents.

What is claimed is:

1. A method for detecting a blending level of biodiesel fuel in an internal combustion engine comprising the steps of:

setting at least two post injection fuel quantity reference values respectively for known biodiesel blending percentage levels;

evaluating a post injection fuel quantity value;

comparing the post injection fuel quantity value with the at least two post injection fuel quantity reference values; and using a predetermined correlation set of values between the post injection fuel quantity value and a biodiesel blending level expressed by biodiesel percentage with respect to a petro-diesel to determine the biodiesel blending level.

2. The method according to claim 1, wherein evaluating is carried out during a regeneration phase of a diesel particulate filter connected to the internal combustion engine to evaluate a post injection fuel quantity value necessary for reaching an inlet temperature desired value of the diesel particulate filter.

3. The method according to claim 2, wherein the post injection fuel quantity value is evaluated on a basis of:
   a base map post injection fuel quantity value; and
   a correction post injection quantity value derived by comparing the inlet temperature desired value of the diesel particulate filter and a current inlet temperature value of the diesel particulate filter.

4. The method according to claim 1, wherein using comprising using the predetermined correlation set of values that is substantially linear in order to allow interpolation of values.

5. The method according to claim 1, wherein setting at least two post injection fuel quantity reference values comprises setting at least two post injection fuel quantity reference values for known biodiesel blending levels respectively expressed in percentage with respect to the petro-diesel.

6. The method according to claim 5, wherein setting at least two post injection fuel quantity reference values comprises setting two post injection fuel quantity reference values of 5% and 100% for the known biodiesel blending levels with respect to the petro-diesel.

7. The method according to claim 6, further comprising determining the biodiesel blending level by interpolation of values using the formula:

$$B_{XX} = \left( \frac{0.95}{QREF_{B100} - QREF_{B05}} \cdot (Q_{Bxx} - QREF_{B05}) + 0.05 \right) \cdot 100$$

wherein $Q_{Bxx}$ is the post injection fuel quantity value, $QREF_{B05}$ and $QREF_{B100}$ are the at least two post injection fuel quantity reference values for the known biodiesel blending levels.

8. The method according to claim 1, wherein the steps of evaluating to comparing are repeated continuously in order to achieve a continuous detection of the biodiesel blending level.

9. The method according to claim 1, wherein evaluating the post injection fuel quantity value is performed by data available to an electronic control unit of the internal combustion engine.

10. The method according to claim 1, wherein the biodiesel blending level is used for monitoring an oil life of the internal combustion engine.

11. The method according to claim 1, wherein the biodiesel blending level is used for controlling a regeneration strategy of a diesel particulate filter.

12. The method according to claim 1, wherein the biodiesel blending level is used for generating a statistical model of soot accumulation of a diesel particulate filter.

13. A computer program product, comprising a non-transitory computer usable medium having a computer readable program code embodied therein, the computer readable program code adapted to be executed to implement a method for for detecting a blending level of biodiesel fuel in an internal combustion engine, the method comprising the steps of:
   setting at least two post injection fuel quantity reference values respectively for known biodiesel blending percentage levels;
   evaluating a post injection fuel quantity value;
   comparing the post injection fuel quantity value with the at least two post injection fuel quantity reference values; and
   using a predetermined correlation set of values between the post injection fuel quantity value and a biodiesel blending level expressed by biodiesel percentage with respect to a petro-diesel in order to determine the biodiesel blending level.

14. The computer program product according to claim 13, wherein evaluating is carried out during a regeneration phase of a diesel particulate filter connected to the internal combustion engine to evaluate a post injection fuel quantity value necessary for reaching an inlet temperature desired value of the diesel particulate filter.

15. The computer program product according to claim 14, wherein the post injection fuel quantity value is evaluated on a basis of:
   a base map post injection fuel quantity value; and
   a correction post injection quantity value derived by comparing the inlet temperature desired value of the diesel particulate filter and a current inlet temperature value of the diesel particulate filter.

16. The computer program product according to claim 13, wherein using comprises using the predetermined correlation set of values that is substantially linear in order to allow interpolation of values.

17. The computer program product according to claim 13, wherein setting at least two post injection fuel quantity reference values comprises setting at least two post injection fuel quantity reference values for known biodiesel blending levels respectively expressed in percentage with respect to the petro-diesel.

18. The computer program product according to claim 17, wherein setting at least two post injection fuel quantity reference values comprises setting the at least two post injection fuel quantity reference values of 5% and 100% for the known biodiesel blending levels with respect to the petro-diesel.

19. The computer program product according to claim 18, wherein the method further comprises determining the biodiesel blending level by interpolation of values using the formula:

$$B_{XX} = \left( \frac{0.95}{QREF_{B100} - QREF_{B05}} \cdot (Q_{Bxx} - QREF_{B05}) + 0.05 \right) \cdot 100$$

wherein $Q_{Bxx}$ is the post injection fuel quantity value, $QREF_{B05}$ and $QREF_{B100}$ are post injection fuel quantity reference values for the known biodiesel blending levels.

20. An electronic control unit (ECU) for an internal combustion engine comprising:
   a digital central processing unit; and
   a storage memory electrically connected to the digital central processing unit, wherein the storage memory stores a computer program adapted to be executed by the digital central processing unit to implement a method for detecting a blending level of biodiesel fuel in the internal combustion engine, the method comprising the steps of:
   setting at least two post injection fuel quantity reference values respectively for known biodiesel blending percentage levels;
   evaluating a post injection fuel quantity value;
   comparing the post injection fuel quantity value with the at least two post injection fuel quantity reference values; and
   using a predetermined correlation set of values between the post injection fuel quantity value and a biodiesel blending level expressed by biodiesel percentage with respect to a petro-diesel in order to determine the biodiesel blending level.

* * * * *